(12) United States Patent
Bach

(10) Patent No.: US 7,207,780 B2
(45) Date of Patent: Apr. 24, 2007

(54) MULTIPLE PORT DUAL DIAMETER PUMPS

(75) Inventor: David T. Bach, Ellicott City, MD (US)

(73) Assignee: Scientific Products and Systems, Baltimore, MD (US)

( * ) Notice: Subject to any disclaimer, the term of this patent is extended or adjusted under 35 U.S.C. 154(b) by 241 days.

(21) Appl. No.: 10/965,287

(22) Filed: Oct. 14, 2004

(65) Prior Publication Data
US 2005/0135952 A1    Jun. 23, 2005

Related U.S. Application Data

(60) Provisional application No. 60/511,566, filed on Oct. 15, 2003.

(51) Int. Cl.
F04B 43/12 (2006.01)

(52) U.S. Cl. .................. 417/53; 417/500; 417/442

(58) Field of Classification Search ........... 417/442, 417/461, 469, 493, 490, 494, 498, 500, 53; 222/253, 309, 249, 384
See application file for complete search history.

(56) References Cited

U.S. PATENT DOCUMENTS

| | | | | |
|---|---|---|---|---|
| 4,203,459 A | * | 5/1980 | Boschung | 137/119.03 |
| 4,464,098 A | * | 8/1984 | Olson | 417/397 |
| 6,244,291 B1 | * | 6/2001 | Hughes | 137/312 |
| 6,511,085 B2 | * | 1/2003 | Sawai | 280/124.157 |
| 6,666,666 B1 | | 12/2003 | Gilbert et al. | 418/9 |
| 6,739,478 B2 | | 5/2004 | Bach et al. | 222/1 |

OTHER PUBLICATIONS

Copending U.S. Appl. No. 10/848,817.

* cited by examiner

*Primary Examiner*—Ehud Gartenberg
*Assistant Examiner*—Vikansha Dwivedi
(74) *Attorney, Agent, or Firm*—Clifford Kraft

(57) ABSTRACT

A multiple port, dual diameter piston fluid dispensing pump which includes multiple input and output ports accessed by rotating at least one of the pistons and a dual or multiple diameter piston or set of pistons that cooperate so that they follow each other. The dispensing piston is of smaller diameter than the pushing piston. This diameter difference permits a longer, controllable stroke to dispense micro-liters of fluid accurately.

11 Claims, 4 Drawing Sheets

MULTIPLE PORT DUAL DIAMETER PUMPS

This application is related to and claims priority from U.S. provisional patent application No. 60/511,566 filed Oct. 15, 2003. Application No. 60/511,566 is hereby incorporated by reference.

BACKGROUND

1. Field of the Invention

The present invention relates generally to fluid pumps and more particularly to multiple port, dual diameter fluid pumps.

2. Description of the Prior Art

Multiple port linear pumps have been used in the biosciences as a means to dispense different fluids from the same pump. Multiple ports also provide the capability to rinse the pump between dispensing strokes. For example, U.S. Pat. No. 6,666,666 shows such a pump. Prior art pumps however have single pistons of fixed diameter. To dispense micro-liter quantities of fluid, they require extremely tiny strokes. This leads to inaccuracy.

What is badly needed is a multiple port, dual or multiple diameter pump for the dispensing of fluids where microliters can be dispensed with a reasonably controllable length stroke.

SUMMARY OF THE INVENTION

The present invention relates to a multiple-port, dual-diameter piston pump that has a top piston having a first diameter and a second bottom piston having a second diameter smaller than the first diameter. The first and second pistons cooperate with each other to load and dispense fluid. This cooperation can be achieved by having a spring or magnet hold the pistons together on the up-stroke with a direct contact push on the down-stroke. Any other method of cooperation or coupling between the pistons is within the scope of the present invention. The pump can have several input ports, the input ports being selected by rotation of at least one of the pistons. The pump also can have several output ports, the output ports also being selected by rotation of at least one pistons. Usually the pistons rotate together; however, this is not a requirement. The first and second pistons operate to cause fluid to be drawn into one of the input ports and dispensed from one of the output ports. The pump can have the pistons coupled with a spring, with magnets or otherwise. The lower or smaller piston can be partially contained in the upper or larger piston.

Various figures and illustrations have been presented to better explain the present invention. The scope of the present invention is not limited to the figures.

DESCRIPTION OF THE INVENTION

Multiple port positive displacement pumps offer the biosciences the capability of having multiple pump capability in one pump. The use of as many as nine or more ports in one pump allows a single pump to be connected to an eight channel pipettor where each of the eight channel volumes can be individually adjusted. At least one of the multiple port pump ports can be an inlet port. The inlet port can be attached to a buffer solution used for washing any of the output channels. When a multiple port pump is designed, it is necessary to provide adequate distance between each of the pump ports in order to make an effective seal. The distance between ports is related to the fluid properties being pumped and that of the fluid internal pressure developed as the pump is used. A typical pump could have around 7 mm spacing between ports with port apertures of around 2.3 mm diameter. The piston diameter for such a pump could be around 30 mm. For this particular example, the effective surface area for the piston is around 706.5 square mm. Different ports can be accessed by simply rotating the piston.

When a pump with a piston of around 30 mm is used, a piston movement of around 1 mm can result. This would result in around 706 micro-liters of fluid being dispensed. The dispensing of small micro-liter volumes could require a linear piston motion of around 7 microns. It is very hard to control such a small linear motion.

The present invention solves this problem by using a dual or multi diameter piston and chamber on a multiple inlet/outlet pump. This greatly diminishes the piston effective area. For example, if the primary piston is around 30 mm in diameter, the face surface area is around 706.5 square mm. If the second diameter of the dual diameter piston is only around 28 mm, the surface area is around 615.1 square mm. This results in the dispensing of only around 91.1 microliters of fluid for each 1 mm of piston travel. The motion for a 5 micro-liter dispense would thus be around 55 microns. The difference between the two piston diameters can be further reduced to enhance small volume multiple port dispensing. Piston arrangements with more than two diameters are within the scope of the present invention.

Figure 1:
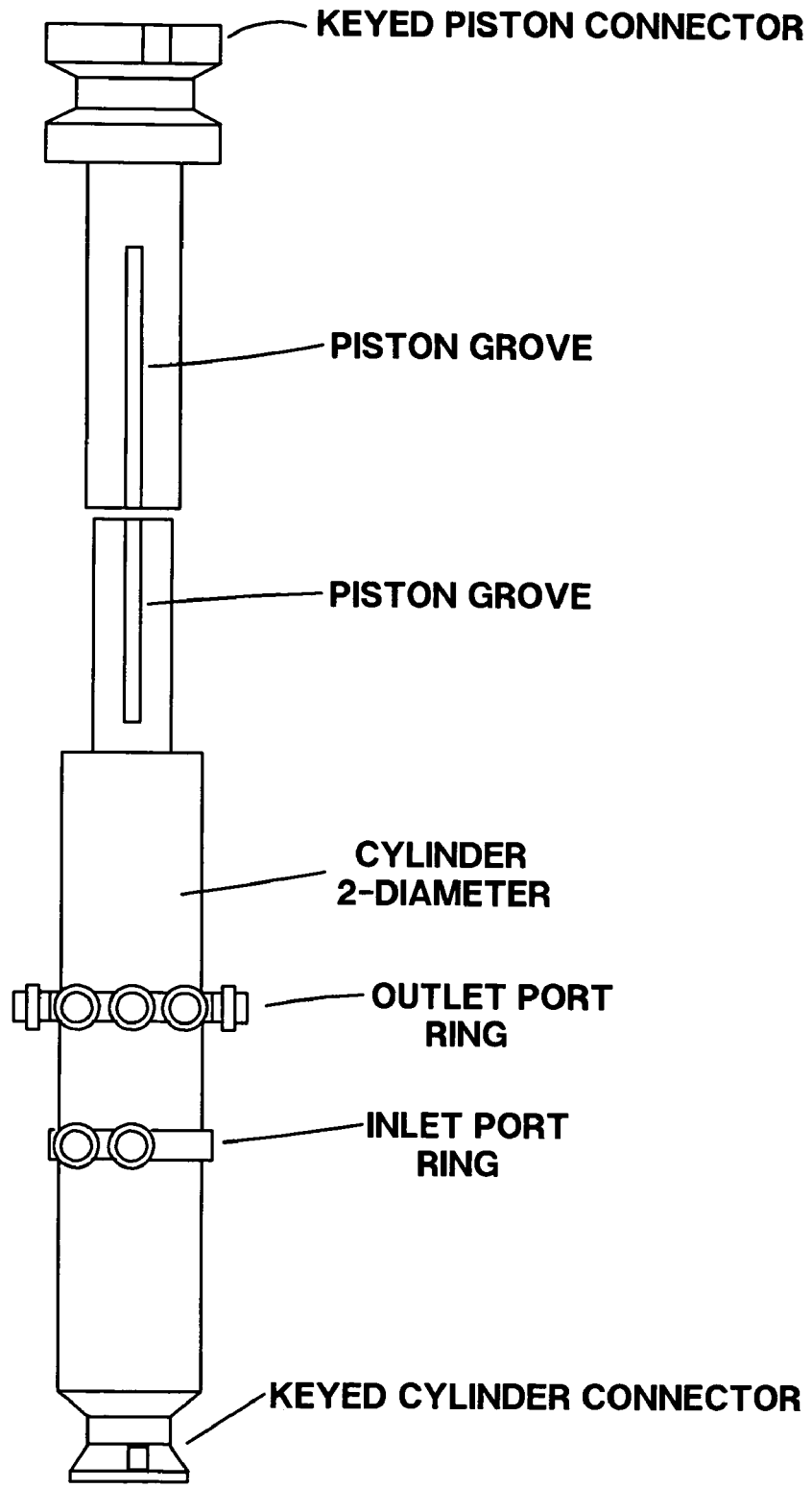
FIG. 1 shows a two diameter piston pump.

FIG. 1 shows a pump with two piston diameters configured in one piston as a single piece. This pump has multiple input and output ports. A piston groove on the larger and smaller pistons is used to keep them aligned.

Figure 2:
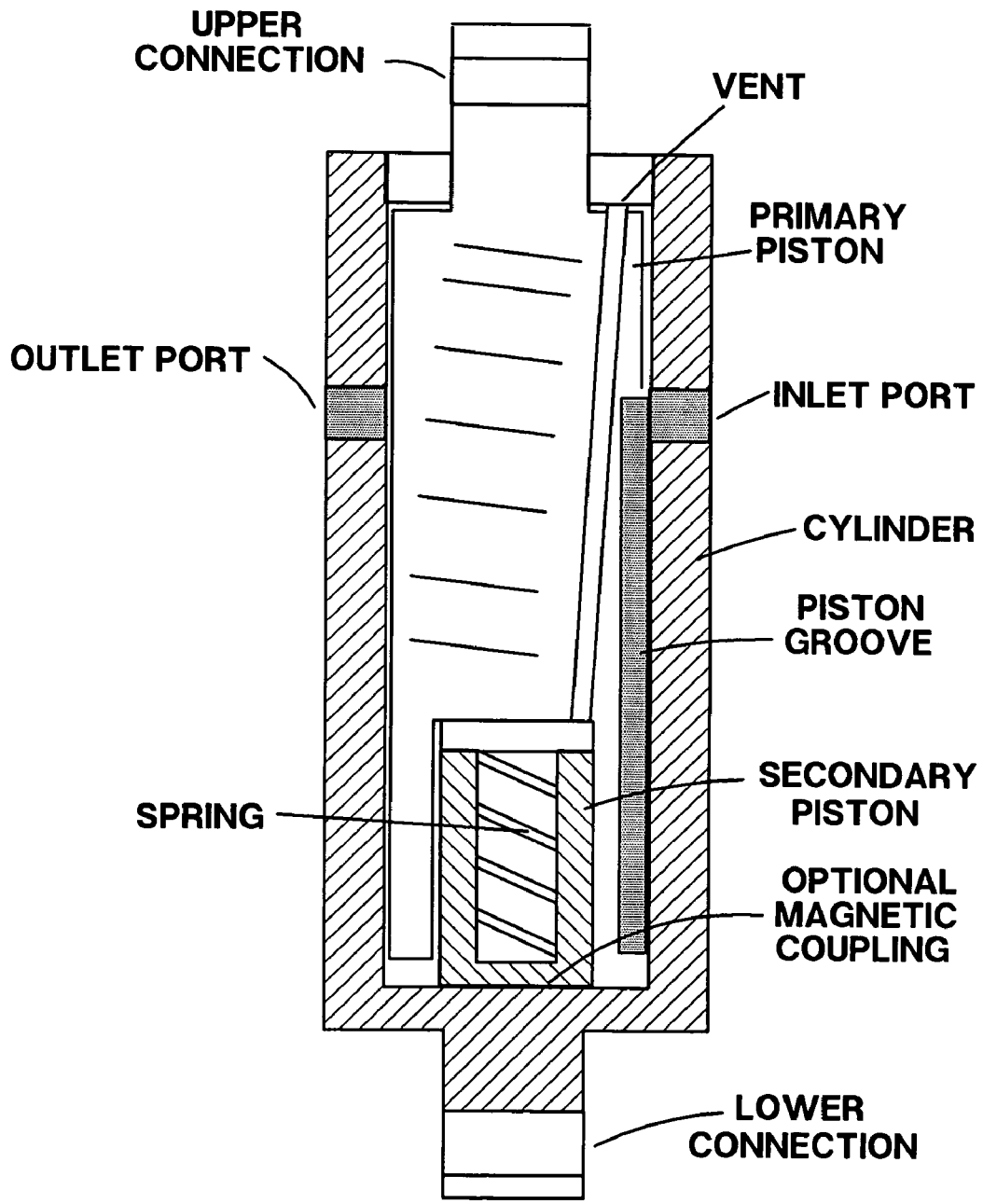
FIG. 2 shows a rotary positive displacement pump with two diameters with piston spring coupling. Here one piston is partially within the other.

FIG. 2 shows a cross-section of a pump with two piston diameters configured in a piston-in-a-piston approach where the internal piston can be spring loaded. Here the spring is used to keep the pistons together on the up-stroke, and direct contact is used to push them together on the down-stroke.

Figure 3:
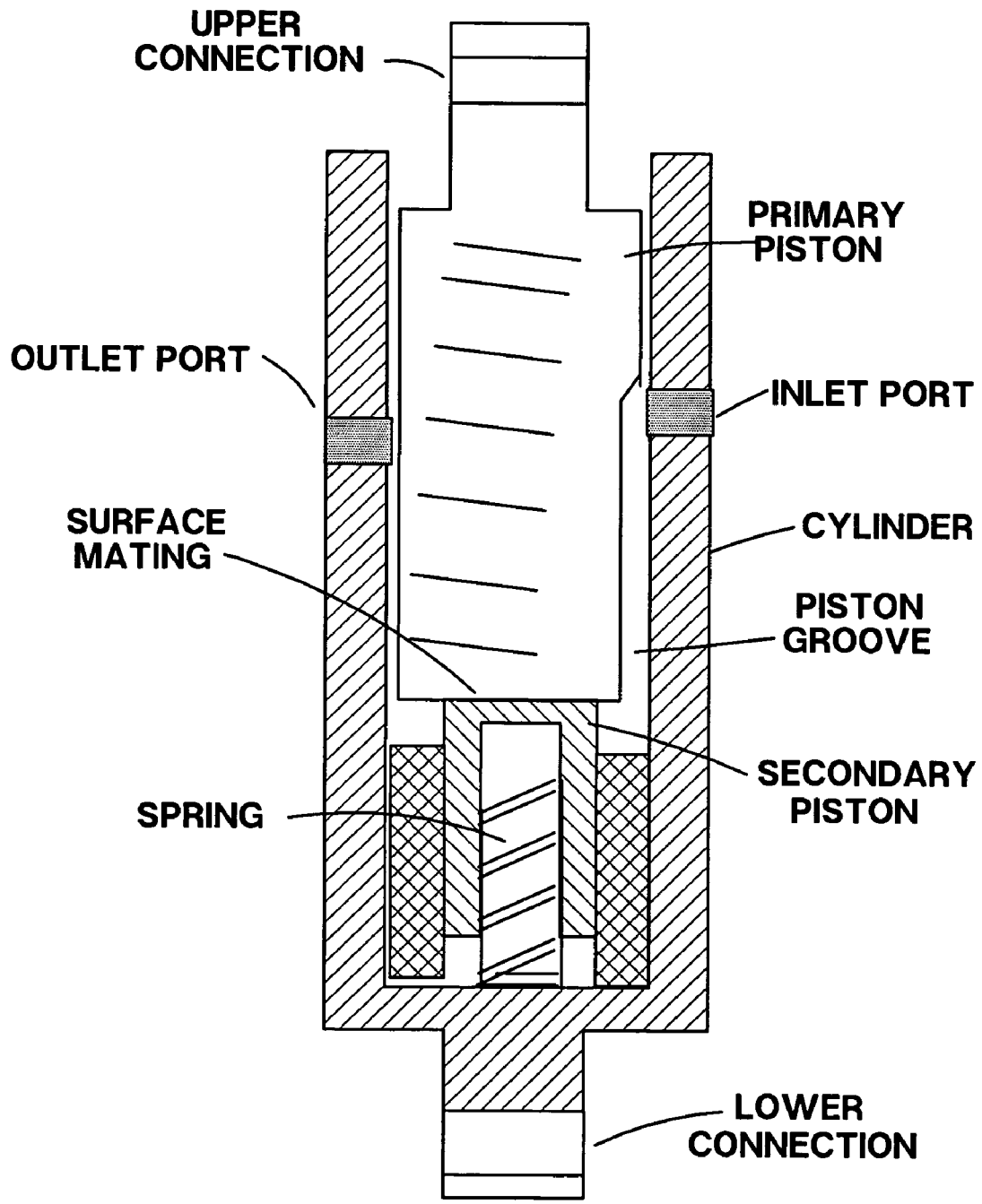
FIG. 3 shows a different embodiment of a two diameter pump with spring coupling.

FIG. 3 shows a cross-section of a pump where one of the pistons is located in line with the primary piston and is also spring loaded. This embodiment functions in a manner similar to the embodiment of FIG. 2.

Figure 4:
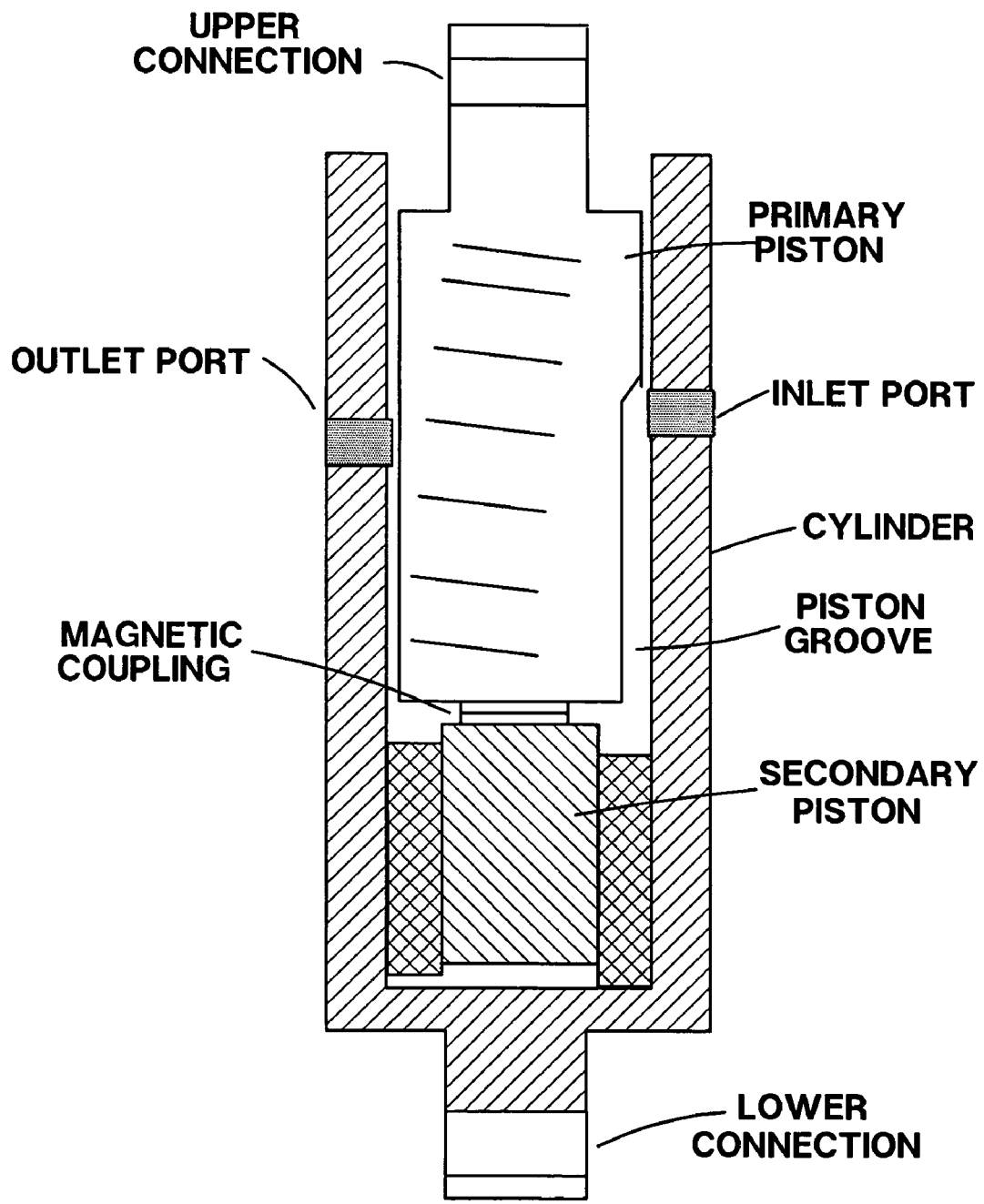
FIG. 4 shows an embodiment with magnet coupling.

FIG. 4 shows a cross-section of a pump where one of the pistons is located in line with the primary piston and is magnetically coupled to it. Here, the two pistons cooperate with each other by being held together with the two magnets. In this arrangement, it is easy to separate the two pistons for cleaning.

The various pump configurations shown in FIGS. 1–4 can be fabricated out of various materials such as stainless steel, ceramic, glass or plastic. Any rigid material can be used to construct such a pump and is within the scope of the present invention. It is preferred that the material used be immune to corrosion or chemical reaction with the fluid being dispensed.

The secondary piston can follow the primary piston making the pump's entire stroke volume equal to the area difference between the two diameters times the stroke length. However, it is not necessary that the secondary piston follow the primary piston throughout the entire stroke. The defined movement of the secondary piston can be anywhere from very small to that of the entire stroke. Optionally, the secondary piston can have a convex curvature where it meets the primary piston thus minimizing the amount of contact area.

Various descriptions and illustrations have been presented to better aid in understanding the present invention. One skilled in the art will understand that many changes and variations are possible. All such changes and variations are within the scope of the present invention.

I claim:

1. A multiple-port, dual-diameter piston pump comprising:
    a first piston having a first diameter;
    a second piston having a second diameter smaller that said first diameter;
    a plurality of input ports, said input ports being selected by rotation of at least one of said first and second piston;
    a plurality of output ports, said output ports being selected by rotation of at least one of said first and second piston;
    said first and second piston being coupled to each other during upstroke motion with a spring or magnet;
    said first and second piston cooperating to cause fluid to be drawn in one of said input ports and dispensed from one of said output ports.

2. The pump of claim 1 wherein said pistons are coupled with a spring.

3. The pump of claim 1 wherein said pistons are coupled by magnets.

4. The pump of claim 1 wherein said second piston is partially contained within said first piston.

5. The pump of claim 1 wherein said pistons are stainless steel.

6. The pump of claim 1 wherein said pistons are plastic.

7. A method of dispensing micro-liters of fluid comprising;
    providing a pump with multiple input and output ports and at least two pistons of different diameters, said pistons cooperating to move linearly to dispense fluid, one of said pistons being a lower piston of smaller diameter than the other of said pistons, said two pistons being coupled to each other during upstroke motion with a spring or magnet;
    rotating at least one of said pistons to an input port location;
    moving said pistons linearly in a direction to load fluid into said pump from said input port;
    rotating at least one of said pistons to an output port location;
    moving said pistons linearly in a direction to dispense fluid from said output port.

8. The method of claim 7 wherein said pistons are stainless steel.

9. The method of claim 7 wherein said pistons are plastic.

10. The method of claim 7 wherein said pistons are spring-coupled.

11. The method of claim 7 wherein said pistons are magnetically coupled.

* * * * *